United States Patent
Yachia et al.

(10) Patent No.: US 11,351,341 B2
(45) Date of Patent: Jun. 7, 2022

(54) URINE FLOW SYSTEM AND METHOD OF USE

(71) Applicant: INNOVENTIONS LTD., Or Akiva (IL)

(72) Inventors: Daniel Yachia, Herzlia (IL); Valentin Ponomarenko, Haifa (IL)

(73) Assignee: INNOVENTIONS LTD., Or Akiva (IL)

(*) Notice: Subject to any disclaimer, the term of this patent is extended or adjusted under 35 U.S.C. 154(b) by 435 days.

(21) Appl. No.: 15/574,921

(22) PCT Filed: May 19, 2016

(86) PCT No.: PCT/IL2016/050531
§ 371 (c)(1),
(2) Date: Nov. 17, 2017

(87) PCT Pub. No.: WO2016/185478
PCT Pub. Date: Nov. 24, 2016

(65) Prior Publication Data
US 2018/0161542 A1  Jun. 14, 2018

Related U.S. Application Data

(60) Provisional application No. 62/163,398, filed on May 19, 2015.

(51) Int. Cl.
*A61M 25/01* (2006.01)
*A61M 25/04* (2006.01)
(Continued)

(52) U.S. Cl.
CPC ....... *A61M 25/0127* (2013.01); *A61F 2/0018* (2013.01); *A61M 25/04* (2013.01);
(Continued)

(58) Field of Classification Search
CPC .......... A61M 25/04; A61M 2210/1085; A61M 2210/1089
See application file for complete search history.

(56) References Cited

U.S. PATENT DOCUMENTS 4,738,667 A * 4/1988 Galloway ............. A61M 25/04
604/530
6,626,876 B1 * 9/2003 Bolmsjo ............... A61F 2/0022
600/574

(Continued)

*Primary Examiner* — Catharine L Anderson
*Assistant Examiner* — Arjuna P Chatrathi
(74) *Attorney, Agent, or Firm* — Robert G. Lev

(57) ABSTRACT

Disclosed is a bladder drainage apparatus comprising a tube including a hollow interior extending through the tube, a flexible anchor, which behaves spring-like, connected to or at one end of the tube, and a magnetic member connected to or at the other end of the tube. The tube is moveable when the magnetic member is engaged by an external magnetic force, creating magnetic traction, and moving the tube, e.g., outward (from its original position, where the sphincter is typically closed), such that it holds open a sphincter, allowing urine to drain from the bladder, to the urethra, to outside of the body. When the external magnetic force is released, the magnetic engagement is terminated, and the force of the flexible anchor pulls the tube back to its original position, whereby the sphincter is again closed, and accordingly urine flow is stopped or otherwise limited.

18 Claims, 11 Drawing Sheets

(51) Int. Cl.
*A61F 2/00* (2006.01)
*A61M 27/00* (2006.01)

(52) U.S. Cl.
CPC ... *A61M 27/008* (2013.01); *A61M 2210/1085* (2013.01); *A61M 2210/1089* (2013.01)

(56) References Cited

U.S. PATENT DOCUMENTS

| | | | |
|---|---|---|---|
| 8,192,419 B2* | 6/2012 | Li | A61J 15/0038 604/500 |
| 8,758,329 B2* | 6/2014 | Paulen | A61M 25/0017 604/544 |
| 2002/0151923 A1* | 10/2002 | Holzer | A61F 2/0022 606/193 |
| 2004/0049170 A1* | 3/2004 | Snell | A61M 25/04 604/544 |

* cited by examiner

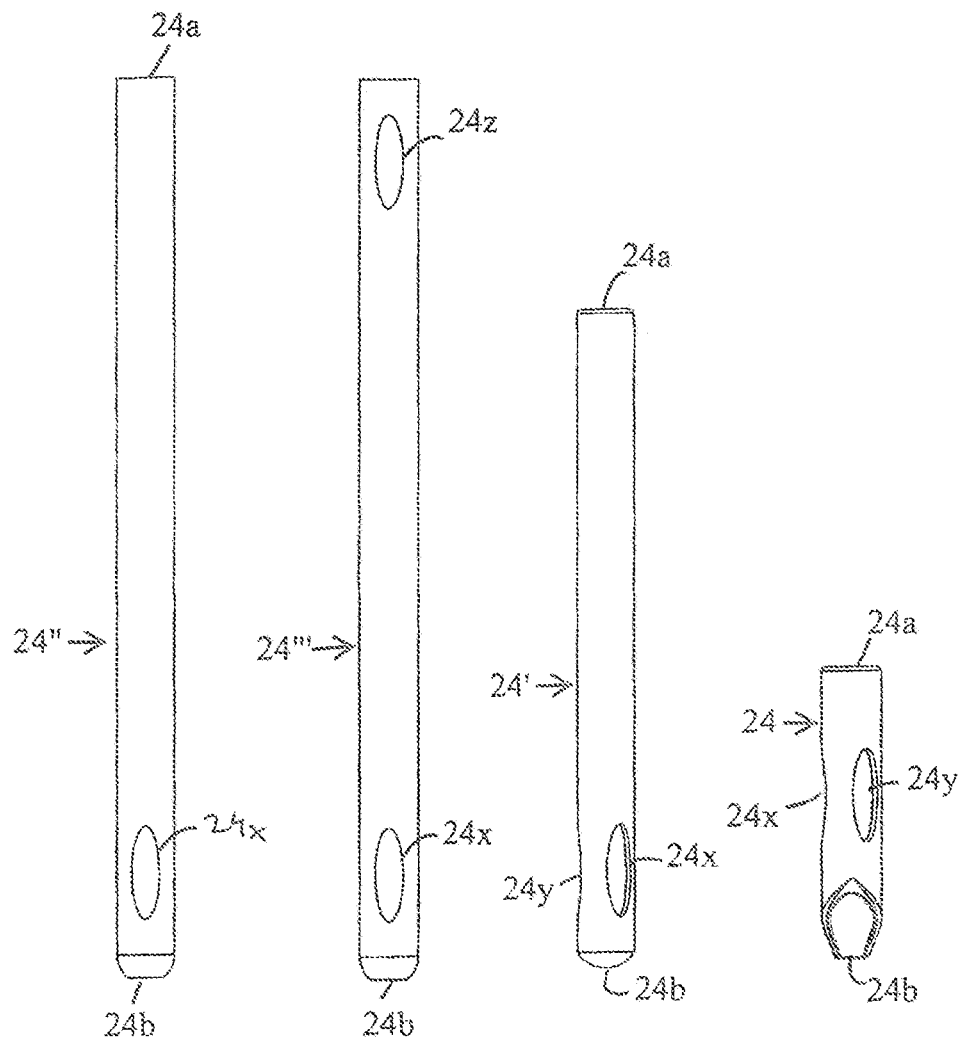

URINE FLOW SYSTEM AND METHOD OF USE

CROSS REFERENCES TO RELATED APPLICATIONS

This application is related to and claims priority from commonly owned U.S. Provisional Patent Application Ser. No. 62/163,398, entitled: Urine Flow System and Method of Use, filed on May 19, 2015, the disclosure of which is incorporated by reference herein in its entirety.

TECHNICAL FIELD

The present invention is directed to devices for assisting urination.

BACKGROUND

Urinary retention is often caused by neurological disorders or by obstructions at the bladder outlet. Neurogenic urinary retention is a condition in which a person is unable to empty the urinary bladder voluntarily due to a neurological dysfunction like damage to the spinal cord or the nerves innervating the urinary bladder and/or of the urinary sphincter. Neurogenic urinary retention is due to an inability of the bladder to contract and/or of the urinary sphincter to relax.

Patients who have spinal cord injuries, multiple sclerosis, Parkinson's disease, or trauma to the pelvic region or intrinsic neurological dysfunction of the bladder or sphincteric muscle may suffer from neurogenic urinary retention on a permanent or transient basis. Some patients may have a bladder/sphincter dyssynergia—instead of relaxation of the sphincter it contracts at the time of bladder contraction and increase the pressure in the bladder that can damage the kidneys. Additionally patients may have a bladder outlet obstruction caused by benign or malignant prostate gland enlargement or urethral strictures. In chronic obstructions the bladder cannot empty itself and the gradually increasing residual urine cause a chronic urinary retention—the inability to empty the bladder and remain with large quantities of residual urine after urination, a condition that may cause damage to the kidneys.

Patients suffering from urinary retention generally have limited options for draining their bladders. These include using a permanently inserted Foley catheter, intermittent catheterization, and a suprapubic drainage tube. All three options have high infection rates, are inconvenient for the patient and/or care giver, are uncomfortable for the patient, and typically cause the patient emotional distress.

SUMMARY

The present invention provides devices (apparatus), systems and methods for allowing patients with neurologic or chronic obstructive urinary retention to drain their bladders, by allowing the passage of urine from the bladder to the urethra, while opening the bladder outlet, which obstructs urine flow. The apparatus and systems of the present invention are usable by both males and females.

Disclosed is a bladder drainage apparatus comprising a tube including a hollow interior extending through the tube, a flexible anchor, which behaves spring-like, connected to or at one end of the tube, and a magnetic member connected to or at the other end of the tube. The tube is movable when the magnetic member is engaged by an external magnetic force, creating magnetic traction, and moving the tube, e.g., outward (from its original position, where the sphincter is typically closed), such that it holds open a sphincter, allowing urine to drain from the bladder, to the urethra, and ultimately leave the body. When the external magnetic force is released, the magnetic engagement is terminated, and the force (e.g., spring-biasing force) of the flexible anchor pulls the tube back (e.g., inward) to its original position. The sphincter is now closed, and urine flow has been stopped or otherwise limited.

Embodiments of the invention are directed to a urinary drainage system. The system comprises an apparatus. The apparatus comprises: a tube including a hollow interior and oppositely disposed first and second ends, a first opening at the first end in communication with the hollow interior, and a second opening at the second end in communication with the hollow interior; an anchor in communication with the first end of the tube allowing for movement of the tube in the body, the anchor for maintaining the apparatus in the body; and, a magnetic member in communication with the second end of the tube, the magnetic member for moving toward another magnetic member during a magnetic engagement (e.g., magnetic traction pulling the magnetic member outward), such that the tube moves from a first position to a second position during the magnetic engagement and to back to the first position from the second position when the magnetic engagement is terminated.

Optionally, the urinary drainage system additionally comprising: a longitudinal axis extending through the hollow interior of the tube, and the tube, when moving between first position and the second position, moves along the longitudinal axis. Optionally, the anchor includes a portion which exhibits spring-like behavior allowing the tube to move between the first and second positions, the first position where the anchor is in a relaxed position and the second position where the anchor is in an expanded position. Optionally, the magnetic member includes a first magnet. Optionally, the urinary drainage system additionally comprises: a second magnet for creating the magnetic engagement with the first magnet so as to move the tube from the first position to the second position.

Optionally, the magnetic engagement is of a force sufficient to open urinary sphincters. Optionally, the anchor includes a coil member including a central point, wherein the coil member communicates with the tube from the central point. Optionally, the coil member is formed of wire.

Optionally, the coil member is of an outer diameter greater than a bladder opening to the urethra.

Optionally, the anchor includes a plurality of members including oppositely disposed first and second ends, the first ends coiled to provide the anchor with the spring-like behavior and the second ends for communication with the tube.

Optionally, the members are made of at least one of wires, ribbons and strips. Optionally, the outer diameter is defined by the members along their peripheries, and this outer diameter is greater than the diameter/length of the bladder opening to the urethra. Optionally, the urinary drainage system additionally comprises: an insertion device configured for receiving the apparatus and delivering the apparatus into the body. Embodiments of the invention are directed to methods for the drainage of urine, for example, from the bladder. The methods comprise initially providing an apparatus. The apparatus comprises: a tube including a hollow interior and oppositely disposed first and second ends, a first opening at the first end in communication with the hollow interior, and a second opening at the second end in communication with the hollow interior; an anchor in communication with the first end of the tube for maintaining the tube in a body cavity, such that the tube is moveable in the body cavity; and, a magnetic member in communication with the second end of the tube, the magnetic member for moving toward another magnetic member during a magnetic engagement such that the tube moves from a first position to a second position during the magnetic engagement and to back to the first position from the second position when the magnetic engagement is terminated. The apparatus is then positioned in the urinary tract, such that the anchor is at least partially within the bladder and the tube is in a first position at least partially in the urethra, and the urinary sphincter is closed.

Optionally, the method additionally comprises applying a magnetic force to the magnetic member to cause movement of the tube from the first position to a second position, where in the second position, the tube moves through the urinary sphincter and opens the urinary sphincter, allowing drainage of urine from the bladder into the urethra, to outside of the body.

Optionally, the applying the magnetic force includes moving a magnet into a magnetic engagement with the magnetic member.

Optionally, the positioning of the apparatus in the urinary track is performed with an insertion device.

Optionally, the method additionally comprises: moving the magnet so as to terminate the magnetic engagement, causing the tube to move from the second position to the first position.

Optionally, the magnet is moved outside of the body.

Other embodiments of the invention are directed to methods for creating urine flow. These methods comprise: placing a tube including a hollow interior and openings in communication with the hollow interior, the openings, disposed at a first end and a second end of the tube, where at least a portion of the tube is in a closed position in the urethra proximate to the bladder and the urinary sphincter is closed; and, applying a force on the tube to move the tube into an open position, past the urinary sphincter, opening the urinary sphincter, the tube including portions on opposite sides of the urinary sphincter, the tube creating a passageway for urine from the bladder to the urethra beyond the urinary sphincter for leaving the body. The force is, for example, a magnetic force, but may also be a mechanical (pulling) force, or other suitable pulling forces.

Optionally, the tube is in communication with a magnetic member, and the tube is moved from the closed position to the open position by magnetic forces when a magnet is positioned with respect to the magnetic member to create a magnetic engagement with the magnetic member.

Optionally, the tube returns to the closed position from the open position, when the magnet is positioned such that the magnetic engagement is terminated.

Optionally, the magnet is positioned outside of the body.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE DRAWINGS

Some embodiments of the invention are herein described, by way of example only, with reference to the accompanying drawings, where like reference numerals or characters represent corresponding or like elements. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

Attention is now directed to the drawing figures where like reference numerals or characters refer to corresponding or like components. The drawing figures are as follows.

FIGS. 5A, 5B, 5C and 5D show front views of tubes used with the disclosed apparatus;

DETAILED DESCRIPTION OF THE DRAWINGS

Figure 1A:
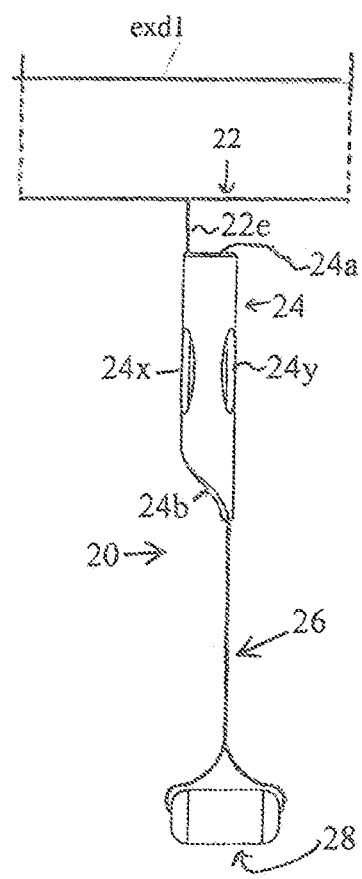
FIGS. 1A and 1B show front and perspective views of an embodiment of an apparatus in accordance with the invention.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

Throughout this document, references to directions, such as upward, downward, inward, outward, and the like, are made. These directional references are to typical orientations for the various apparatus and systems of the invention. They are exemplary only, and not limiting in any way, as they are for description and explanation purposes.

Figure 1B:
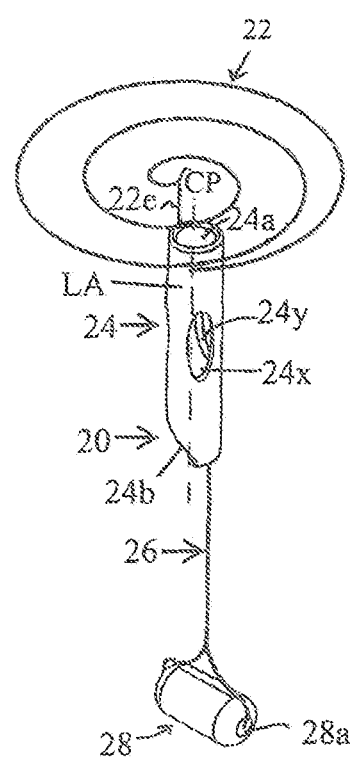

FIGS. 1A and 1B show an apparatus 20 in accordance with an embodiment of the invention. The apparatus 20 includes a coil (coil member) or anchor 22, which is flexible. The coil 22 connects to a tube 24. A cord 26 attaches the tube 24 to a magnetic or magnetizable member 28.

The coil 22, is, for example, a spring, or a member that exhibits spring-like behavior, and is designed to rest in contact with the bladder wall to anchor the apparatus 20 in the bladder and posterior urethra. The coil 22 is, for example, of a diameter (exd1 of FIG. 1A) greater than the diameter/length of the bladder opening to the urethra, to limit travel or movement of the coil 22 in the bladder, and holding the apparatus 20 in the body, during movement of the tube 24 by external forces, as detailed below. The coil 22 is made of, for example, surgical grade materials, and is, for example, a wire, such as nitinol, coated with an inert material, such as silicone, such that the coil 22 behaves as a spring with the inert coating preventing or minimizing the deposition or urinary salts.

The coil 22 includes an extension cord 22e, which extends from a center point CP. The extension cord 22e connects to the tube 24.

The tube 24 is designed to move within the urethra, and is of a length to move past the external sphincter, allowing urine to pass from the bladder to the urethra downstream of the sphincter. The tube 24 is hollow in its interior and open at both ends 24a, 24b (this end 24b is shown, for example, as angled or curved). The tube 24, for orientation purposes, includes a longitudinal axis (LA in broken lines in FIG. 1B) extending through the interior. The ends 24a, 24b of the tube 24 include, for example, one or more openings 24x, 24y, that along with the cylindrical shape of the tube 24, allow for the passage of urine to the urethra, for drainage of the bladder. The openings 24x, 24y may be positioned anywhere on the tube 24, and one or more openings are permissible The openings 24x, 24y, may be oval, as shown, rounded, circular, rectangular or the like, to allow the passage of urine therethrough. At least two openings are spaced apart from each other at a distance greater than the width of the sphincter (e.g., 406 in FIGS. 9A and 9B), to allow urine to pass through the sphincter, from the bladder, through the tube 24, to the urethra for exiting the body. Alternate tubes suitable for use with the apparatus detailed herein do not need to have openings (for example, tube 24 of FIGS. 7A and 7B).

The tube 24 is, for example, cylindrical in shape, as shown, but other shapes are also permissible. The length of the tube 24 is variable, based on the operations desired to be performed. The tube is made of materials, such as silicone, polyurethane, or other materials from which urethral catheters are made of.

The cord 26 is of an inert material to the body as well as being non-magnetic. A material for the cord 26 is, for example, polypropylene. The cord 26, for example, extends through a bore 28a in the magnetic or magnetizable member 28, but may be attached to the magnetic or magnetizable member 28 by other suitable mechanical or chemical fasteners, or combinations thereof.

The magnetic member 28 is, for example, a magnet, of materials such as Neodymium IronBoron (NeFeB). Magnetized or magnetizable materials like iron are also suitable for the magnetic member 28, as are one or more magnets within a casing, mounting or the like, attached to the cord 26.

While a magnetic force is typically used with the magnetic member 28, other forces such as mechanical forces, pulling forces and the like may also be used with the magnetic member or the cord 26, to move the tube 24 between the positions disclosed herein, to allow for bladder drainage.

Figure 2A:
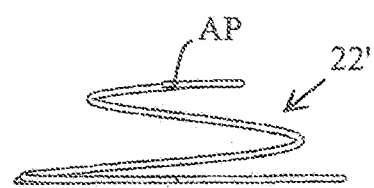
FIGS. 2A and 2B show front and perspective views, respectively, of alternative spring-like members for the apparatus of FIGS. 1A and 1B.
Figure 2B:
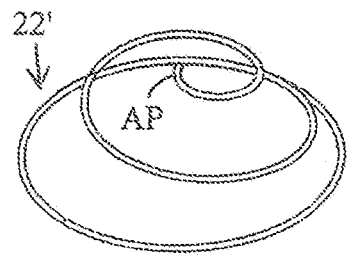
Figure 3A:
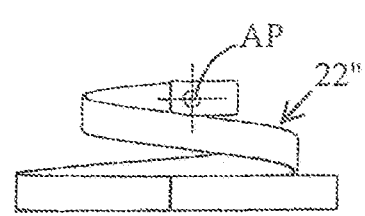
FIGS. 3A and 3B show front and perspective views, respectively, of other alternative spring-like members for the apparatus of FIGS. 1A and 1B.
Figure 3B:
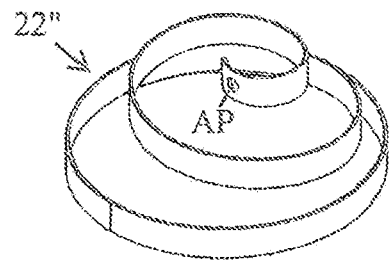
Figure 4A:
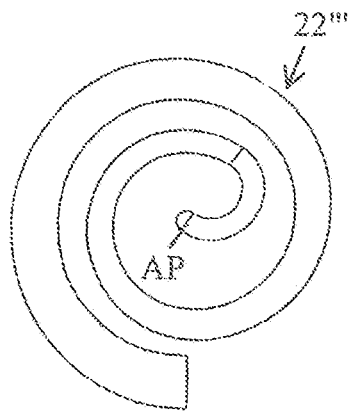
FIGS. 4A and 4B show front and perspective views, respectively, of another alternative spring-like members for the apparatus of FIGS. 1A and 1B.
Figure 4B:
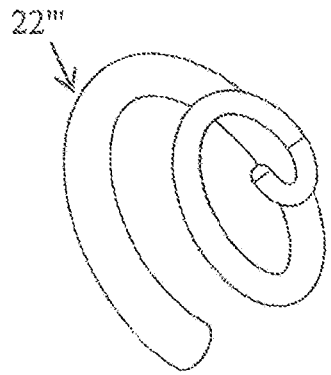

FIGS. 2A and 2B, 3A and 3B, and, 4A and 4B, show alternate members 22', 22" and 22'", which are in coiled arrangements of, for example, wires, ribbons or strips, and tubes, of various materials, which act as springs or act to exhibit spring-like behavior, and are usable as the coil or anchor 22 of the apparatus 20. FIGS. 2A and 2B show a wire coil 22', with an attachment point AP for a cord (similar to cord 26, but of an appropriate length). FIGS. 3A and 3B show a ribbon or strip coil 22", of a material such as nitinol, with an attachment point AP for a cord (similar to cord 26). FIGS. 4A and 4B show an inflatable member coil 22'", of a material such as nylon, polyethylene terephthalate (PET), cross-linked polyethylene, with an attachment point AP for a cord (similar to the cord 26).

FIGS. 5A, 5B, 5C and 5D show tubes suitable for the apparatus 20, 120, 220, 320 of the present invention. FIG. 5A shows the tube 24 of the apparatus 20. FIGS. 5B, 5C and 5D show tubes 24', 24", 24'" of different lengths with openings 24x, 24y. Tube 24'" has an additional opening 24z (one opening 24z is shown but multiple opening are also permissible) at the opposite end 24a of the tube 24'". These tubes 24', 24", 24'" are similar in construction to the tube 24, except their ends 24b are different.

Figure 6A:
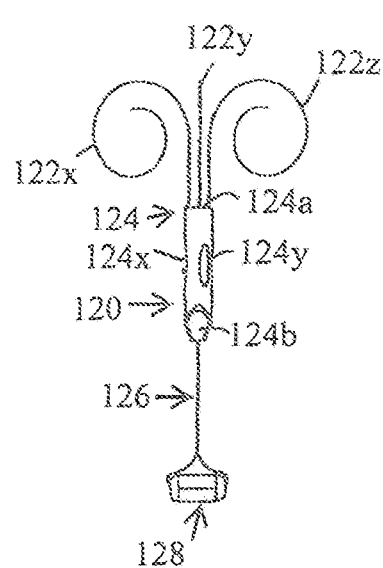
FIGS. 6A and 6B show front and perspective views of an alternative embodiment of an apparatus in accordance with the invention.
Figure 6B:
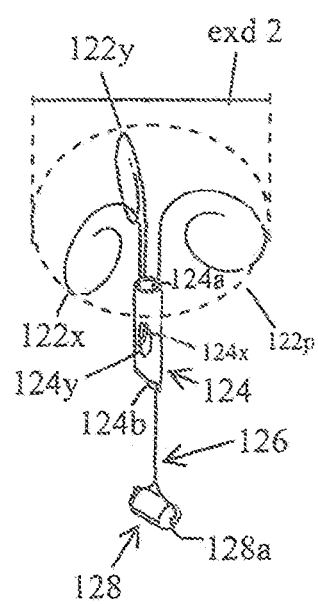

FIGS. 6A and 6B show an alternative apparatus 120, similar to the apparatus 20, with similar or identical components or elements, to those of the apparatus 20, increased by "100" In the apparatus 120, the coil 22 has been replaced with two or more wire coils 122x, 122y, 122z, for example, of the same material as the coil 22, and attached to the tube 124, by conventional fastening means and techniques. The wire coils 122x, 122y, 122z, define a periphery 122p (in broken lines) of a diameter (exd2 in FIG. 6B) greater than the diameter/length of the bladder opening to the urethra. This larger diameter of the coils 122x, 122y, 122z (collectively based on the periphery 122p), limits travel or movement of the coils 122x, 122y, 122z (confining them to the bladder/bladder neck), so as to define the anchor for the apparatus 120, in the bladder. Accordingly, the coils 122x, 122y, 122z can hold the apparatus 120 in the body, during movement of the tube 124 by external forces (e.g., magnetic forces/magnetic traction), such that the apparatus 20 is not pulled out of the body, as detailed below. The tube 124, cord 126 and magnetic member 128 are, for example, in accordance with the tube 24, cord 26 and magnetic member 28, detailed for the apparatus 20 above.

The multiple wire coils or inflatable member coils 122x, 122y, 122z, in this arrangement provide the apparatus 120 with a collective spring-like behavior. Accordingly, this apparatus 120 functions similarly to the apparatus 20, which is detailed further below.

Figure 7A:
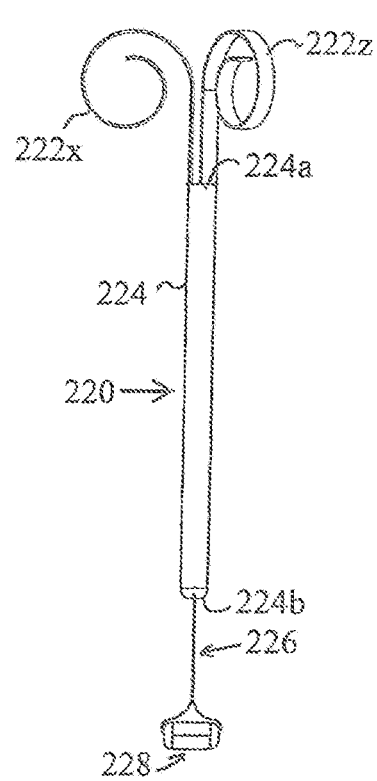
FIGS. 7A and 7B show front and perspective views of another alternative embodiment of an apparatus in accordance with the invention.
Figure 7B:
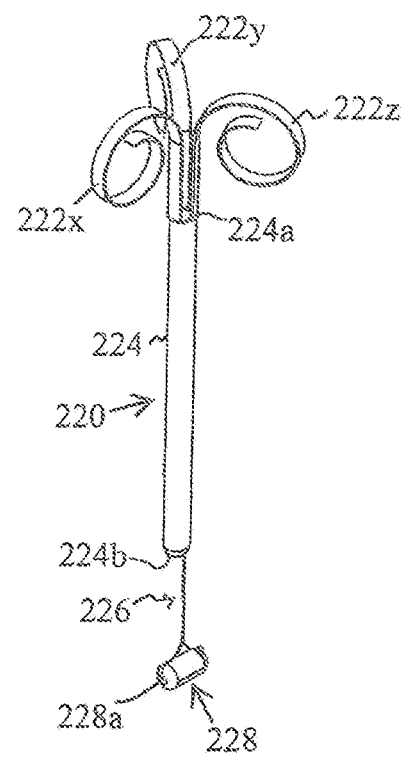

FIGS. 7A and 7B show an alternative apparatus 220, similar to the apparatus 20, with similar or identical components or element, to those of the apparatus 20, increased by "200." In this apparatus 220, the coil 22 has been replaced with ribbon or strip coils 222x, 222y, 222z, for example, of a resilient material, for example, nitinol, which behaves in a spring-like manner. The ribbon coils 222x, 222y, 222z are attached to the tube 224, by conventional fastening means and techniques. The cord 226 and magnetic member 228 are in accordance with the cord 26 and magnetic member 28 detailed for the apparatus 20 above.

The multiple ribbon coils 222x, 222y, 222z, in this arrangement, provide the apparatus 220 with a collective spring-like behavior, like the coils 122x, 122y, 122z, of the apparatus 120, detailed above. Accordingly, this apparatus 220 functions similarly to the apparatus 20, which is detailed further below, and the apparatus 120.

Figure 8A:
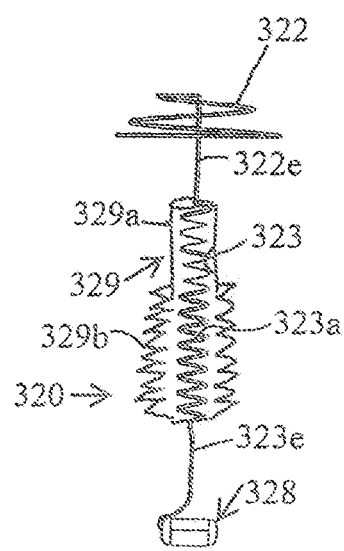
FIG. 8A shows an alternative embodiment of an apparatus in accordance with the invention in a first or relaxed position, with a tube attached.
Figure 8B:
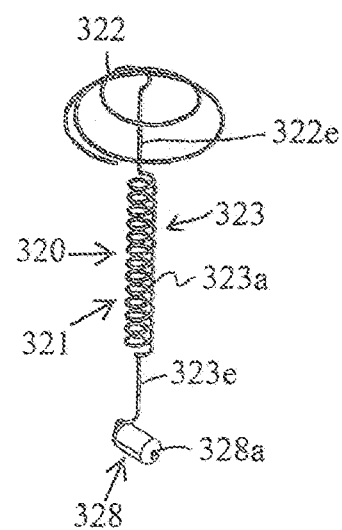
FIG. 8B shows the alternative embodiment of an apparatus of FIG. 7A with the tube removed.

FIGS. 8A and 8B show another alternative apparatus 320, in a relaxed position, prior to extension for bladder drainage. The apparatus 320 includes an integral member 321, for example, of a single piece, which includes a coil 322, a body 323 of a spring 323a, and a cord 326. The integral member 321 is made of materials such as spring steel or nitinol covered by a coating such as silicone, or other non-magnetic materials inert to the body, or other inert materials. The coil 322 is extended, but may also be flat in this "relaxed" position, as shown in FIGS. 1A and 1B, and detailed above. The coil 322 includes an extension 322e that joins to the body 323, and the body 323 includes an extension 323e, which attaches to a magnetic member 328 (similar to magnetic members 28, 128, 228 detailed above). The coil 322 and body 323 of a spring 323a combine to provide the apparatus 320 with spring behavior, in particular at the integral member 321, as discussed above for apparatus 20, 120 and 220.

A tube 329 overlies and attaches to the spring 323, by conventional fastening means and techniques, as shown in FIG. 8A. The integral member 321 serves as a core member for the tube 329. The tube 329 is formed of a flat portion 329a, at its end proximate to the coil 322, and a folded, or accordion-like portion 329b at its downstream end proximate to the magnetic member 328. Alternatively, the entire tube 329 can be folded, with folded and non-folded portions mixed on the tube 329. The tube 329 is made of materials, such as nylon, polyethylene terephthalate (PET), cross-linked polyethylene, and the like, which can accommodate the aforementioned folds.

Figure 9A:
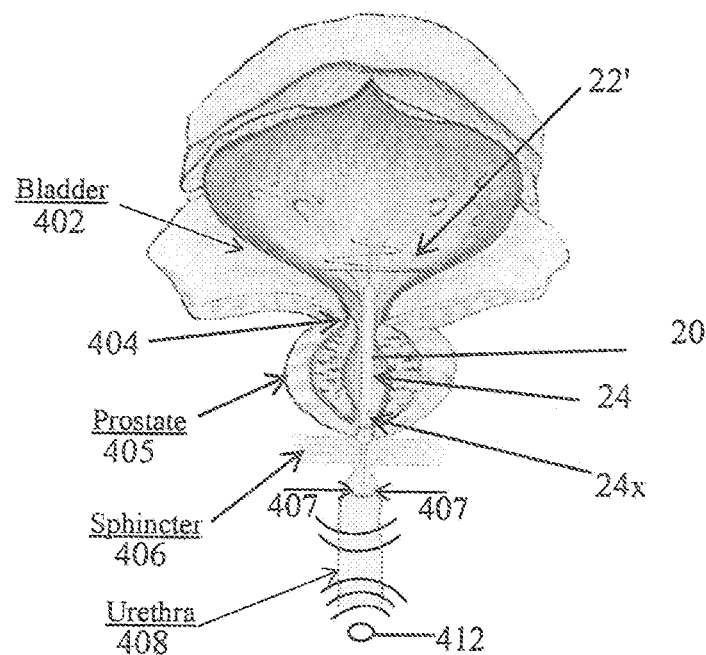
FIGS. 9A and 9B show the apparatus of FIGS. 1A and 1B in an exemplary operation in the urinary tract of the body.
Figure 9B:
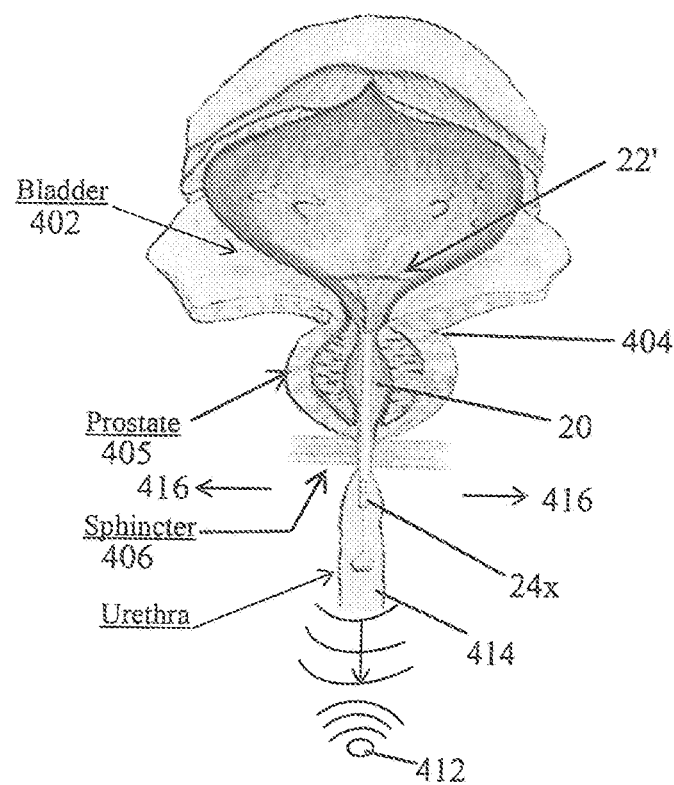

FIGS. 9A and 9B show the apparatus 20 in an exemplary operation, i.e., bladder drainage. (The apparatus 20 is similar to that shown in FIGS. 1A and 1B, and as described above, but the coil 22 is replaced by the coil 22' of FIGS. 2A and 2B). Initially, in FIG. 9A, in a non-drainage position, the apparatus 20 is such that the coil 22' (for example, in an upward funnel orientation) serves as an anchor, and sits in the bladder 402 crossing at the bladder neck 404. The coil 22', with its spring-like behavior, is biased, so as to be in a relaxed or unexpanded position, as the external sphincter as the tube 24 is on one side of the external sphincter 406, which is closed. The tube 24 is partially in the posterior urethra 405, and upstream of (above) the external sphincter 406, which is normally closed (illustrated by the arrows 407), preventing bladder 402 drainage through the urethra 408 (and out of the body (not shown)).

When bladder 402 drainage is desired, a magnet 412 is brought into contact with the body, and into magnetic communication with the magnetic member 28, where magnetic poles of the magnetic member 28 and magnet 412, orient North/South to create a magnetic traction (illustrated by the curved lines). The magnetic traction causes the magnetic member 28 to move downward (outward) in the urethra 408, this movement causes the tube 24 to move in this same direction (the direction of the arrow 414). This also causes the spring-like coil 22' to move from the relaxed position to an expanded position (for example, in a downward funnel orientation). The coil or anchor 22' diameter, which is greater than the diameter/length bladder/urethra opening and/or the bladder neck, limits movement (travel) of the coil or anchor 22' to within the bladder 402, such that the coil or anchor 22' remains in the bladder 402, anchoring the apparatus 20, and the external (magnetic) forces do not pull the apparatus 20 out of the body. The downstream end of the tube 24 moves past the external sphincter 406, opening it (moving it outward in accordance with the arrows 416), such that portions of the tube 24 with openings are on both sides of the sphincter 406, allowing for urine to pass from the bladder 402, through the tube 24 (tubular member) of the apparatus (device) 20 and then through the urethra 408, and out of the body (not shown), resulting in the bladder 402 draining, as shown in FIG. 9B.

When drainage is complete, the magnet is moved out of the magnetic engagement with the magnetic member 28, and the magnetic traction ceases. Once the magnetic traction ceases, the spring force, caused by the biasing of the coil 22', allows the coil 22' to return to the relaxed position, where the tube 24 is pulled to inward, back to the position shown in FIG. 9A, where the sphincter 406 returns to being closed.

Figure 10A:
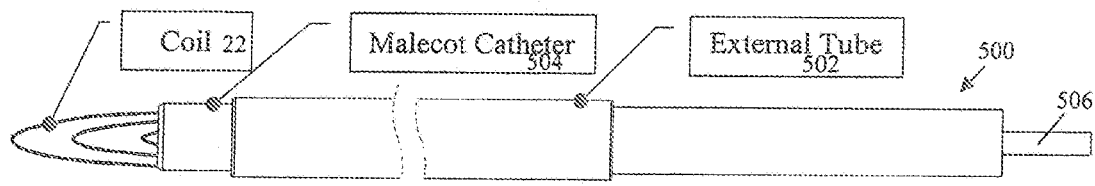
FIG. 10A shows a delivery apparatus for use with the apparatus of the invention.
Figure 10B:
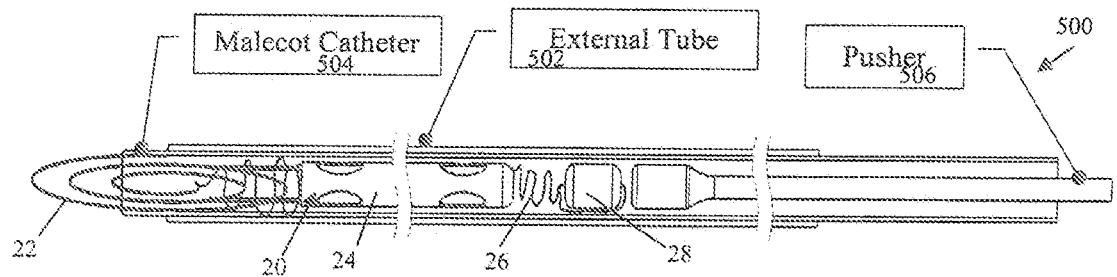
FIG. 10B shows a cut-away view of FIG. 10A with a portion of the delivery apparatus removed.

FIGS. 10A, 10B, 11A, 11B and 12A-12C show an apparatus 500 and a process for delivering the exemplary apparatus 20 (with a coil 22, tube 24 and magnetic member 28, as shown in FIG. 10B, for example) to the site in the bladder and urinary tract. As shown in FIGS. 10A and 10B, the delivery apparatus 500 includes an external tube 502, inside of which is a balloon catheter or a Malecot like (or spacing) catheter 504, as a spacer, a pusher member 506, and the apparatus 20, with the coil 22 positioned distal most in the spacing catheter 504.

Figure 11A:
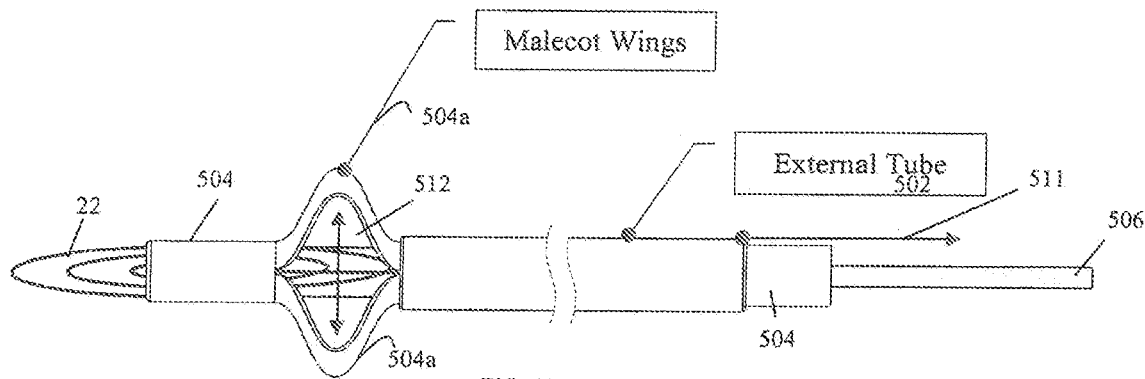
FIG. 11A shows the delivery apparatus of FIG. 10A in an operational position.
Figure 11B:
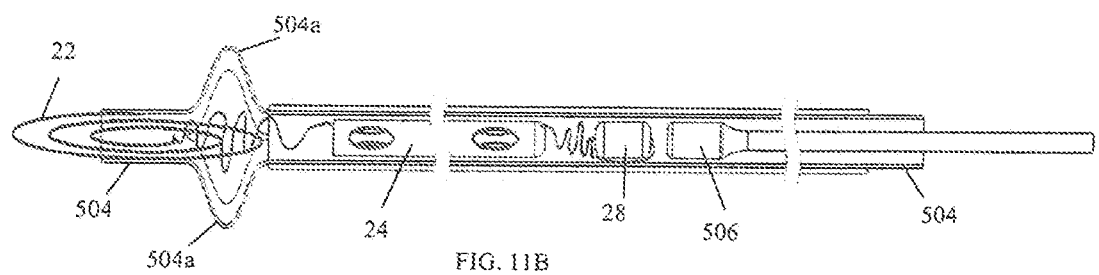
FIG. 11B shows a cut-away view of FIG. 11A with a portion of the delivery apparatus removed.
Figure 12A:
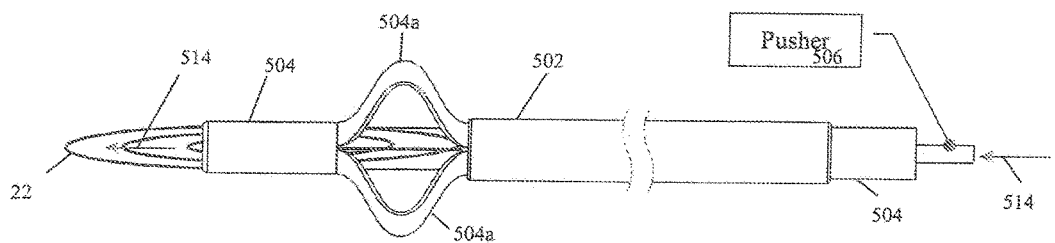
FIG. 12A shows the delivery apparatus of FIG. 10A in an operational position.
Figure 12B:
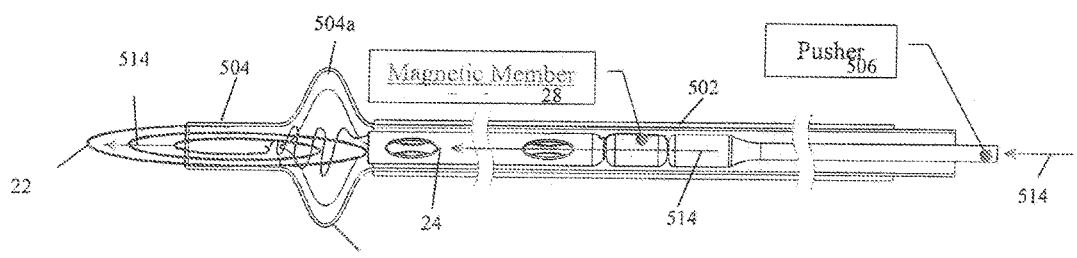
FIG. 12B shows a cut-away view of FIG. 12A with a portion of the delivery apparatus removed.
Figure 12C:
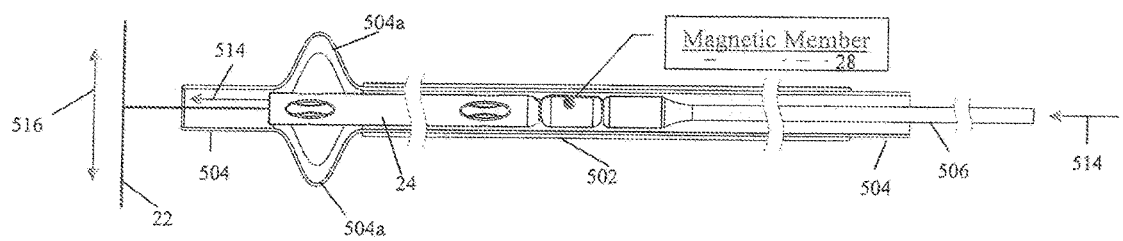
FIG. 12C shows the delivery apparatus of FIG. 10A in an operational position.

The delivery apparatus 500 is moved into the bladder, and the external tube 502 is pulled rearward or proximal. If a balloon spacing catheter is used, the balloon is inflated. If a Malecot-type catheter is used as a spacer, The pull back of the external tube 502 (illustrated by the arrow 511) allows the wings 504a of the spacing catheter 504 to open (in the direction of the double-headed arrow 512), and anchor the delivery apparatus 500 at the bladder neck, as shown in FIGS. 11A and 11B. With the anchoring complete, the pusher member 506 is pushed distally (in the direction of the arrows 514), as shown in FIGS. 12A and 12B, such that the coil 22 emerges from spacing catheter 506, and orients itself in the bladder, the orientation shown by the double headed arrow 516, as shown in FIG. 12C. The delivery apparatus 500 is then retracted.

Figure 13:
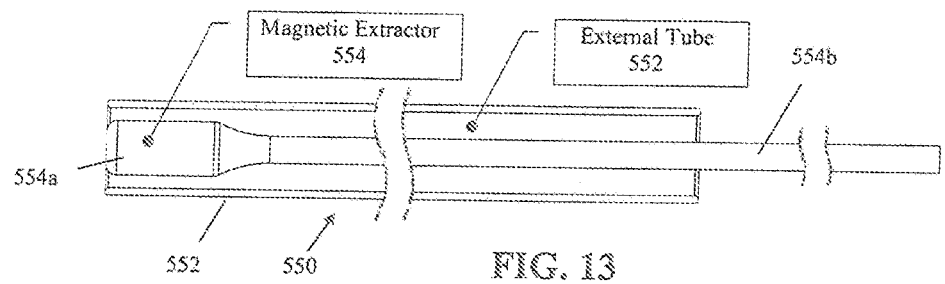
FIG. 13 shows an extraction apparatus for use with the apparatus of the invention.

FIGS. 13-16 detail an extraction apparatus 550 for the apparatus 20, and its operation in removing the apparatus 20 from the bladder and urinary tract. FIG. 13 shows the extraction apparatus 550, formed of an external tube 552 and an extractor 554, for moving in the tube 552. The extractor 554 includes an end 554a, which is magnetic, the remainder of the extractor 554 is, for example, a rod 554b.

Figure 14:
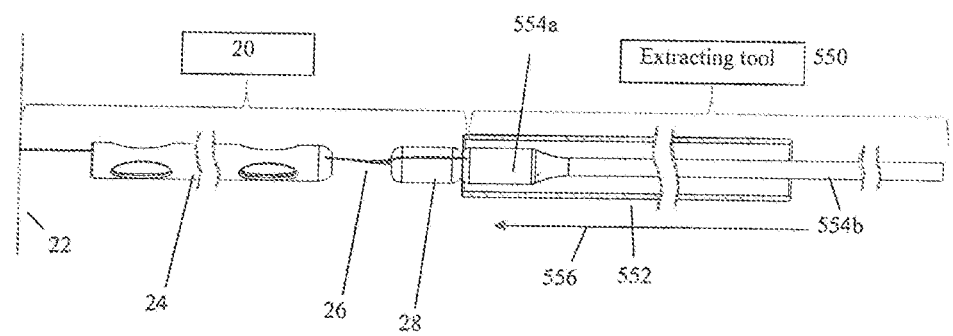
FIG. 14 shows the extraction apparatus of FIG. 13 in operation connecting to the apparatus of the present invention; and, FIGS. 15 and 16 show the extraction apparatus in operational positions.
Figure 15:
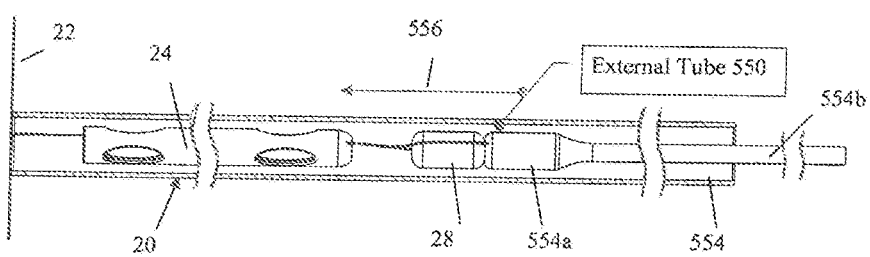

As shown in FIG. 14, the extraction apparatus 550 is inserted into the urinary tract (and moved distally, in the direction of the arrow 556), where the magnetic end 554a of the extractor 554 magnetically attaches to the magnetic member 28 of the apparatus 20. The external tube 552 is pushed forward, in the direction of the arrow 556, until the tube 24 of the apparatus 20 enters the external tube 552, and the edge of the external tube 552 reaches the coil 22 of the apparatus 20, as shown in FIG. 15.

Figure 16:
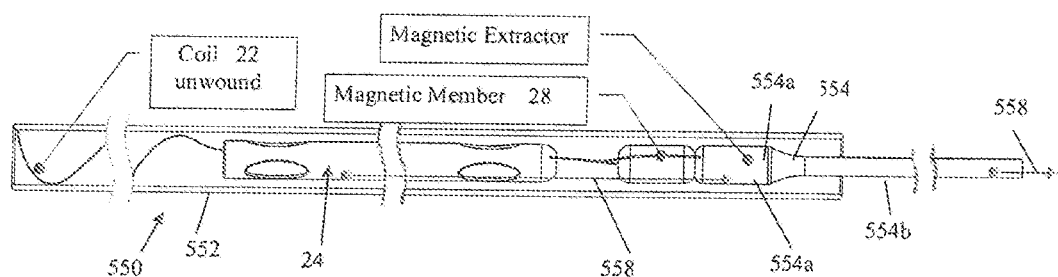

The extractor 554 is now moved rearward or proximally, in accordance with the arrow 558 (the rod 554b is pulled in the proximal or rearward direction). This movement causes the coil 22 to unwind and move into the external tube 552, as shown in FIG. 16. With the coil 22 in the external tube 552, the external tube 552 is removed from the urinary tract.

The present invention is also suitable for animal use.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

What is claimed is:

1. A urinary drainage system comprising:
an apparatus configured to effect intermittent urinary drainage in a body by comprising:
a rigid tube including a hollow interior and oppositely disposed first and second ends, a first opening at the first end in communication with the hollow interior, and a second opening at the second end in communication with the hollow interior;
an anchor configured to be inserted into a urinary bladder, the anchor in communication with the first end of the tube allowing for movement of the tube in the body, the anchor for maintaining the apparatus in the body, the anchor including a portion which exhibits spring-like behavior allowing the tube to move between a first position and a second position, the first position where the anchor is in a relaxed position and the second position where the anchor is in an expanded position; and,
a magnetic member in communication with the second end of the tube, the magnetic member for moving toward another magnetic member during a magnetic engagement such that the tube moves from the first position to the second position during the magnetic engagement and back to the first position from the second position when the magnetic engagement is terminated wherein the anchor remains in the urinary bladder when the tube moves between the first position and the second position.

2. The urinary drainage system of claim 1, additionally comprising: a longitudinal axis extending through the hollow interior of the tube, and the tube, when moving between first position and the second position, moves along the longitudinal axis.

3. The urinary drainage system of claim 1, wherein the magnetic member includes a first magnet.

4. The urinary drainage system of claim 3, additionally comprising: a second magnet for creating the magnetic engagement with the first magnet so as to move the tube from the first position to the second position.

5. The urinary drainage system of claim 3, wherein the magnetic engagement is of a force sufficient to open urinary sphincters.

6. The urinary drainage system of claim 1, wherein the anchor includes a coil member including a central point, wherein the coil member communicates with the tube from the central point.

7. The urinary drainage system of claim 6, wherein the coil member is formed of wire.

8. The urinary drainage system of claim 6, wherein the coil member is of an outer diameter greater than the diameter of the bladder opening to the urethra.

9. The urinary drainage system of claim 1, wherein the anchor includes a plurality of members including oppositely disposed first and second ends, the first ends coiled to provide the anchor with the spring-like behavior and the second ends for communication with the tube.

10. The urinary drainage system of claim 9, wherein the members are made of at least one of wires, ribbons and strips.

11. The urinary drainage system of claim 8, wherein the outer diameter is defined by the members along their peripheries is greater than a bladder opening to the urethra.

12. The urinary drainage system of claim 1, additionally comprising, an insertion device configured for receiving the apparatus and delivering the apparatus into the body.

13. A method for effecting intermittent bladder drainage of urine in a body, said method comprising:
providing and operating an apparatus comprising:
a rigid tube including a hollow interior and oppositely disposed first and second ends, a first opening at the first end in communication with the hollow interior, and a second opening at the second end in communication with the hollow interior;
an anchor configured to be inserted into a urinary bladder, the anchor in communication with the first end of the tube for maintaining the tube in a body cavity, such that the tube is moveable in the body cavity, the anchor including a portion which exhibits spring-like behavior allowing the tube to move between a first position and a second position, the first position where the anchor is in a relaxed position and the second position where the anchor is in an expanded position; and,
a magnetic member in communication with the second end of the tube, the magnetic member for moving toward another magnetic member during a magnetic engagement such that the tube moves from the first position to the second position during the magnetic engagement and to back to the first position from the second position when the magnetic engagement is terminated wherein the anchor remains in the urinary bladder when the tube moves between the first position and the second position; and,
positioning the apparatus in the urinary tract, such that the anchor is at least partially within the bladder and the tube is in the first position at least partially in the urethra, and the urinary sphincter is closed, wherein said rigid tube moves in said urinary tract to start and stop urinary drainage.

14. The method of claim 13, additionally comprising: applying a magnetic force to the magnetic member to cause movement of the tube from the first position to a second position, where the tube moves through the urinary sphincter and opens the urinary sphincter, allowing drainage of urine from the bladder into the urethra, to outside of the body.

15. The method of claim 14, wherein applying the magnetic force includes moving a magnet into a magnetic engagement with the magnetic member.

16. The method of claim 14, wherein the positioning of the apparatus in the urinary track is performed with an insertion device.

17. The method of claim 15, additionally comprising: moving the magnet so as to terminate the magnetic engagement, causing the tube to move from the second position to the first position.

18. The method of claim 15, wherein the magnet is moved outside of the body.

\* \* \* \* \*